United States Patent [19]

Mowery, Jr.

[11] 4,112,743
[45] Sep. 12, 1978

[54] STEP-WISE GRADIENT CARRIER FOR LIQUID CHROMATOGRAPHY

[75] Inventor: Richard A. Mowery, Jr., Bartlesville, Okla.

[73] Assignee: Phillips Petroleum Company, Bartlesville, Okla.

[21] Appl. No.: 723,395

[22] Filed: Sep. 15, 1976

[51] Int. Cl.² .................................. G01N 31/08
[52] U.S. Cl. ................... 73/61.1 C; 23/230 R; 210/31 C; 210/198 C
[58] Field of Search ............ 23/230 R, 253 R; 210/198 C, 31 C; 73/61.1 C, 422 GC

[56] References Cited

U.S. PATENT DOCUMENTS

| 3,373,872 | 3/1968 | Hrdina | 23/253 R UX |
| 3,701,609 | 10/1972 | Bailey | 210/198 C |
| 3,827,302 | 8/1974 | Sato | 73/422 GC |
| 3,847,550 | 11/1974 | Scott et al. | 73/61.1 C X |
| 3,926,809 | 12/1975 | Jones | 210/198 C |
| 3,961,534 | 6/1976 | Gundelfinger | 73/422 GC |
| 3,975,946 | 8/1976 | Ball et al. | 73/422 GC X |

OTHER PUBLICATIONS

Jackson et al., "Solvent Delivery Systems for High Speed LC", American Laboratory, Oct. 1974, pp. 41-51.

*Primary Examiner*—Morris O. Wolk
*Assistant Examiner*—Arnold Turk

[57] ABSTRACT

A process and apparatus for gradient elution by liquid chromatography is provided wherein a second carrier having a composition different from the first carrier is introduced and propelled through the chromatographic apparatus by the first carrier.

13 Claims, 4 Drawing Figures

STEP-WISE GRADIENT CARRIER FOR LIQUID CHROMATOGRAPHY

This invention relates to chromatography.

Liquid chromatography is the oldest form of chromatography, being almost fifty years senior to gas chromatography. Liquid chromatography has, however, remained relatively dormant until recently. During the last decade there has been a rebirth of interest in liquid chromatography, primarily because of improvements in the efficiency of liquid chromatography packing materials. Now termed high speed liquid chromatography (HSLC) or high performance liquid chromatography (HPLC), liquid chromatography has grown as gas chromatography did sometime past. Initially a laboratory instrument, liquid chromatography is increasingly being used in the process field where it is capable of both monitor and control functions.

In many respects, liquid chromatography can be considered as complementary to gas chromatography. There is considerable overlap between the two chromatographic techniques since many compounds can be either vaporized or dissolved. In these cases, gas chromatography is generally the preferred method since gas chromatography is more advanced in its development and will provide an analysis in less effort and lower cost. Liquid chromatography is generally used for the more complex separations involving compounds that are difficult or impossible to separate by gas chromatography. These include compounds which are non-volatile or thermally unstable, which polymerize or react on heating, or which are high boiling and require an excessively high temperature to vaporize. Additionally, liquid chromatography can provide certain unique separations which cannot be carried out by gas chromatography, such as reordering of eluting compounds, separation by compound classes, molecular size distribution, and the separation of ionic species.

It is often desirable to analyze sample mixtures having components that are vastly different and which are impossible to separate using a single carrier in a reasonable time. Components which are unnecessarily retained on the column not only lengthen the analysis time, but also require a higher sample concentration. More importantly, components which fail to readily elute with a chosen mobile phase can appear at a later date, thus providing an incorrect analysis.

In gas chromatography, the column can be temperature programmed to speed up analyses and to sharpen some of the later peaks, thus increasing sensitivity. The liquid chromatographic counterpart of temperature programming is known as "gradient elution". With gradient elution, an analysis starts with carrier solvent A which, during the analysis, is gradually changed in a timed and predictable manner to carrier solvent B. When gradient elution is properly applied, it is possible to separate peaks which could not otherwise be separated with a single carrier or carrier mixture. It is also possible to speed up an analysis for those sample components which are relatively insoluble in carrier solvent A, and to sharpen some of the later peaks.

One approach to gradient elution is incremental gradient elution, wherein the chromatographic column is equilibrated with solvent A and the flow rate is set for the analytical run. The sample is injected and after a suitable period of time, the pump is turned off, the inlet tube is put into a reservoir of solvent B, and the pump is restarted. The process is repeated for each solvent it is desired to use.

In a somewhat more sophisticated system, the gradients are generated in an external reservoir, i.e., mixing chamber, at ambient pressure and then drawn through a high pressure pump to the column. In a yet more sophisticated system, a series of time-proportioning solenoid valves is used to control the ratio of primary and secondary solvents supplied to the high pressure pump.

The advantages of an external gradient system are lower cost and virtually infinite flexibility with respect to the number of solvents and the proportions in which they are mixed. The disadvantages are that such systems are time-consuming. The external mixing chamber, if used, must be cleaned after each analysis.

Another type gradient system employs two pumps that flow into a high pressure mixing chamber prior to going through the column. The major advantages of this type system are rapid turnaround time and amenability to automation. The disadvantages are higher initial cost and higher maintenance cost due to addition of a second high pressure pump and programmer.

An object of the present invention is to provide an apparatus for gradient elution.

Another object of the present invention is to provide a method for gradient elution.

Other objects, aspects and advantages of this invention will be readily apparent to those skilled in the art from the reading of the following disclosure.

In accordance with the present invention there is provided a liquid chromatographic apparatus comprising a chromatographic column, means for detecting a property of the column effluent, means for introducing a first liquid carrier to the column inlet, means for introducing a liquid sample to the column inlet, and means disposed between the column inlet and the first carrier introducing means for introducing a second liquid carrier having a composition different from the first carrier liquid, whereby the second carrier liquid is propelled into and through the column by the first carrier liquid.

Also provided in accordance with the present invention is a novel method for liquid chromatographic analysis which comprises introducing a first carrier liquid, under pressure, into a chromatographic column and through a detecting means, introducing a measured liquid sample into the column, thereby eluting at least a portion of the sample through the column and the detecting means, and after a predetermined interval, introducing a second carrier liquid into the column in place of the first carrier liquid thereby eluting the remainder of the sample through the column and the detecting means, wherein the second carrier liquid is propelled through the column and the detector means by the first carrier liquid.

The apparatus of this invention is particularly suitable for the analysis of liquid mixtures containing compounds having a wide range of capacity factors. Separation of such mixtures is difficult using a single carrier. The compounds having low capacity factors elute easily, but compounds with a high capacity factor are retained on the column longer than is necessary for proper resolution. By changing the polarity or composition of the carrier, it is possible to elute the higher capacity factor compounds in a shorter time.

The invention will be better understood by reference to the drawings of which:

Figure 1:
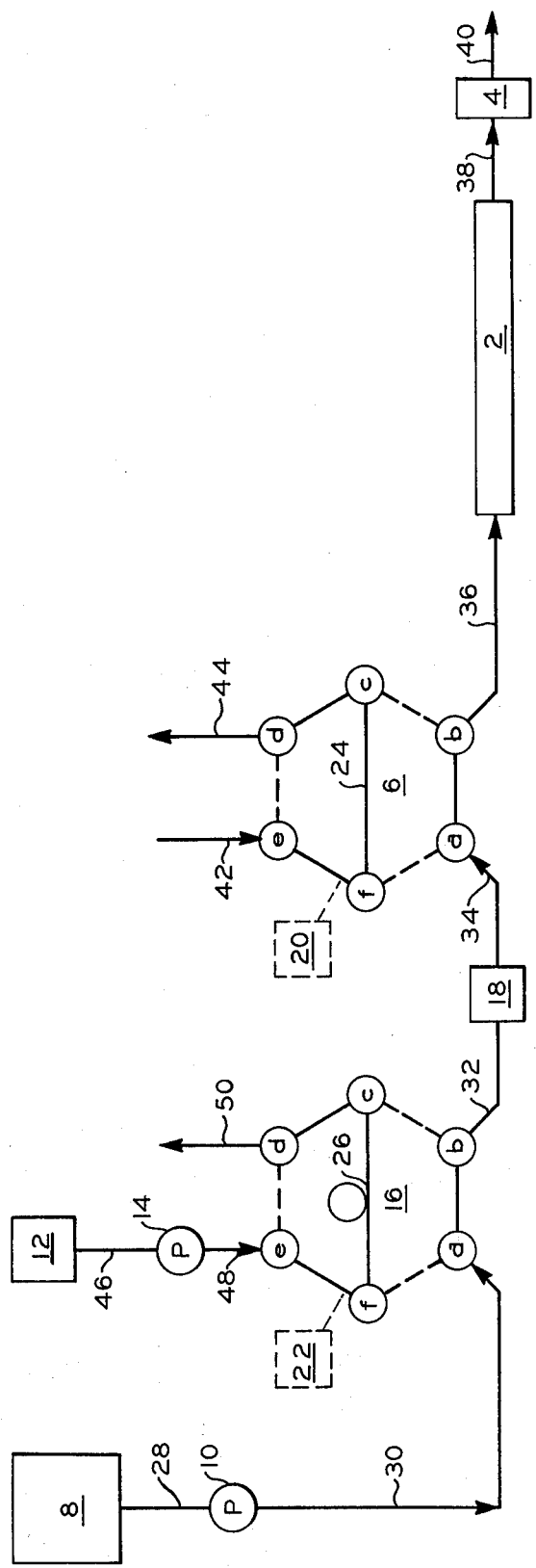
FIG. 1 is a schematic representation of the apparatus of this invention.

Referring now to FIG. 1, the apparatus comprises a chromatographic column 2, detector means 4, sampling valve means 6, first carrier reservoir 8, first pump means 10, second carrier reservoir 12, second pump means 14, carrier valve means 16 and, optionally, mixing chamber 18.

In the embodiment shown in FIG. 1, the sample valve means 6 and the carrier valve means 16 are multi-port, multi-conduit valve means. A suitable multi-port valve means is described in U.S. Pat. No. 3,111,849. The multi-port valve means are shown diagrammatically as six port valves with the small circles representing the ports, the solid straight lines between adjacent ports representing the passages in the first position of the valve, and the dashed straight lines between adjacent ports representing the passages in the second position of the valve. The ports are designated $a$–$f$. In the first position of the valves, port $a$ is connected to port $b$, port $c$ to port $d$ and port $e$ to port $f$. In the second position of the valves, port $a$ is connected to port $f$, port $b$ to port $c$, and port $d$ to port $e$. The sample valve means 6 has actuating means 20 in association therewith for changing the position of the valve means. Carrier valve means 16 has actuating means 22 for the same purpose. These valves are available from the Seiscor Division of Seismography Service Corporation, Tulsa, Okla.

Sample valve means 6 has a sample chamber 24 of fixed volume connected between ports $f$ and $c$. The carrier valve means 16 has a carrier chamber 26 of fixed volume, as later explained, connected between the ports $f$ and $c$.

The first carrier liquid is passed from the first carrier reservoir 8 via conduit means 28 to high pressure pump means 10, such as Haskel Pneumatic Amplifier Pump Model MCP 36, available from Haskel Engineering and Supply Co., Burbank, Calif. While various types of high pressure pumps are available for liquid chromatography, pneumatic amplifier high pressure pumps, capable of operating in either the constant pressure or constant volume mode, are generally less complex and more trouble-free than other type pumps. The pressure on the first carrier liquid is increased by pump means 10 to an elevated pressure. The first carrier liquid, under elevated pressure, is passed from the high pressure pump means 10 via conduit means 30, carrier valve means 16, conduit means 32, mixing chamber 18, conduit means 34, sample valve means 6 and conduit means 36 to the chromatographic column 2.

The chromatographic column 2 contains a partitioning material capable of selectively retarding the flow through such material of the constituents of a sample mixture directed thereto. The effluent from the column 2 is passed via conduit means 38 to a conventional detector means 4. Although not limited thereto, detector means 4 is preferably a high sensitivity detector, such as an ultraviolet light detector capable of accuracy determining the concentrations of constituents of low concentration in the mixture directed to column 2. The effluent from the detector means 4 is withdrawn via vent conduit means 40.

The liquid mixture to be analyzed is passed via conduit means 42 to the sample valve means 6. The liquid mixture is passed through the sample chamber 24 then to a vent conduit means 44. Upon actuation of the sample valve means, the carrier liquid is caused to flow through the sample chamber 24 thereby carrying the sample portion of the liquid mixture via conduit means 36 into the column 2.

The second carrier liquid is passed from the second reservoir 12 via conduit means 46 to low pressure pump means 14 such as pump Model 19-60029-003, available from the Milton Ray Company, St. Petersburg, Fla. The low pressure pump means 14 circulates the second carrier liquid to the carrier chamber 26 via conduit means 48, through the carrier chamber 26, then to vent conduit means 50. Upon actuation of the carrier valve means 16, the first carrier liquid is caused to flow through the carrier chamber 26, thereby propelling the second carrier liquid into the conduit means 32, then through the remainder of the apparatus, as previously described. Although carrier valve means 16 is shown disposed between high pressure pump means 10 and sample valve means 6, it will be apparent to those skilled in the art that carrier valve means 16 can alternatively be disposed between sample valve means 6 and the inlet of column 2.

The volume of the carrier chamber 26 is not critical, although it is presently preferred that such volume be sufficient to completely elute the more difficulty elutable constituents of the sample mixture. It is also presently preferred that the cross-sectional area of the carrier chamber be such that mixing between the first and second carriers will be minimal.

As noted previously, the mixing chamber 18 is optional. When it is desired that the change from the first carrier to the second carrier be abrupt, the mixing chamber 18 is not used. It is, however, within the scope of this invention to carry out gradient elution using the apparatus of this invention, by repeatedly activating and releasing the carrier valve means 16. The ratio of the time activated to the time released will determine the composition produced. The two carriers then mix in mixing chamber 18. A gradient can be produced by changing the time ratio of the two carriers, within the limitations of the valve response time and the mixing time of the carriers.

It is also within the scope of this invention to employ at least one valve means for introducing at least one further carrier liquid having a composition different from the first and second carrier liquids described previously.

The following example illustrates the invention.

EXAMPLE

The apparatus used in this example had the configuration shown in FIG. 1. The high pressure pump 10 was a Haskel Pneumatic Amplifier Pump, Model MCP 36, available from Haskel Engineering and Supply Co., Burbank, Calif. The low pressure pump 14 was Pump Model 19-60029-003, available from the Milton Ray Company, St. Petersburg, Fla. The valve means 6 and 16 were Model VIII high pressure valves, available from the Seiscor Division of Seismograph Service Corporation, Tulsa, Okla. The carrier chamber 26 in carrier valve means 16 was a 5 ft. × ⅛-inch section of stainless steel tubing, and the sample chamber 24 of valve means 6 had a volume of 2 microliters. The chromatographic column 2 was a 1 ft. × ¼-inch section of stainless steel tubing packed with Bondapak C-18, available from Waters Associates, Milford, Mass. The detector 4 was an ultraviolet detector cell available from Laboratory Data Control, Riviera Beach, Fla. The detector cell was referenced to air. The sample analyzed was a mixture of benzene and cumene.

Figure 2:
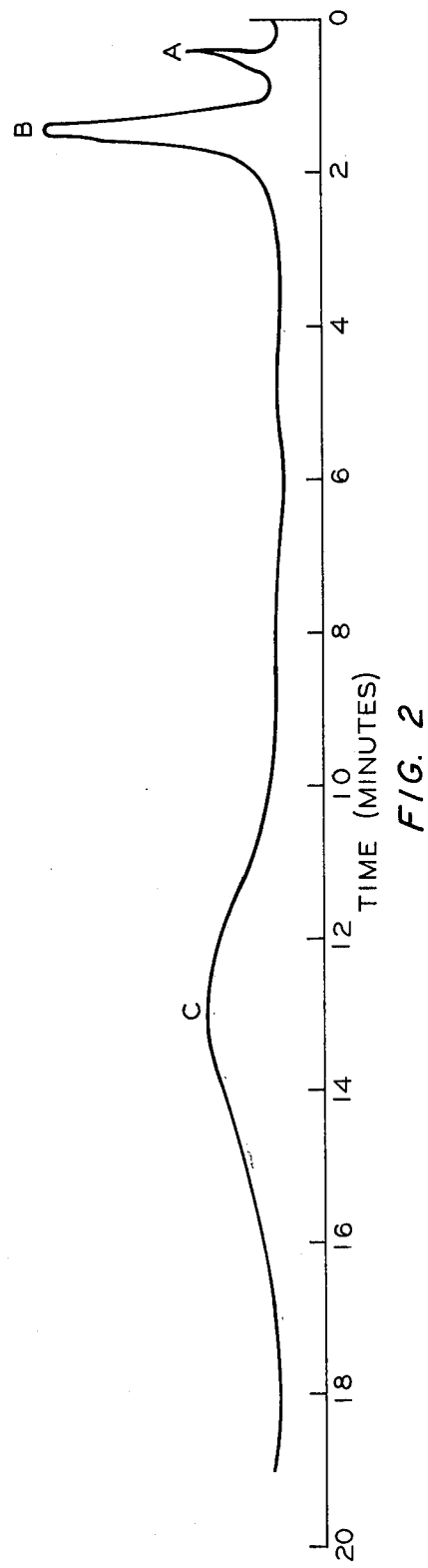
FIG. 2 is a chromatogram showing the separation of benzene and cumene from a sample mixture using a single carrier.

In the first comparison run, the single carrier was a 25% methanol-water solution. Referring to FIG. 2, the sample mixture was injected at time $t_o$. The solvent front (unretained impurities) (Peak A) elutes first, followed by the benzene (Peak B) and the cumene (Peak C). The single carrier was satisfactory for separating the benzene from the sample's solvent front, but the cumene was unnecessarily retained on the column.

Figure 3:
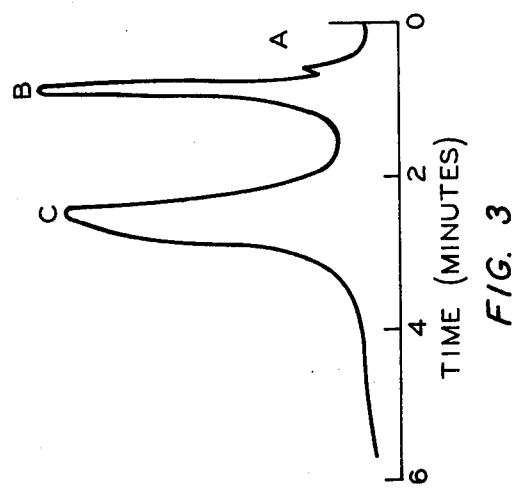
FIG. 3 is a chromatogram showing the separation of benzene and cumene using a different single carrier.

In the second comparison run, the single carrier was a 50% methanol-water solution. Referring to FIG. 3, it can be seen that while the high capacity factor compound, i.e., cumene (Peak C), has moved forward, the low capacity factor compound, i.e., benzene (Peak B), has moved too far forward and is unresolved from the solvent front (Peak A).

Figure 4:
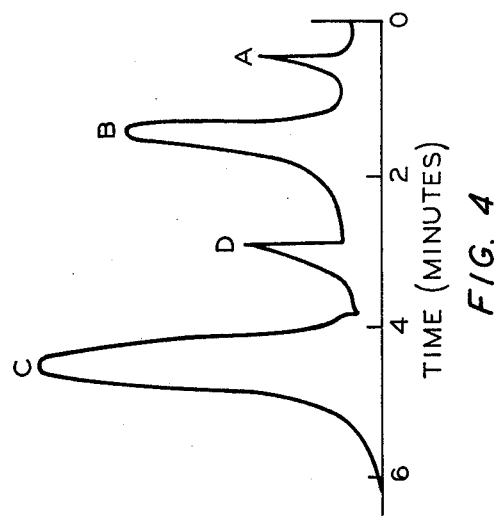
FIG. 4 is a chromatogram showing the separation of benzene and cumene in accordance with the method of this invention.

In the invention run, two carriers were employed, the first carrier being a 25% methanol-water solution and the second carrier being a 50% methanol-water solution. Referring to FIG. 4, the sample was injected at time $t_o$. The solvent front (Peak A) is seen to appear first, followed by the benzene (Peak B). Immediately following elution of the benzene, the carrier valve was switched so that the second carrier liquid, i.e., 50% methanol-water solution, contained in the carrier loop was caused to flow through the column. The Peak D indicates that the solvent front of the second carrier had passed the detector. The change in carrier caused the cumene (Peak C) to elute in a more reasonable time.

Reasonable variations and modifications, which will be apparent to those skilled in the art, can be made in this invention without departing from the spirit and scope thereof.

What is claimed is:

1. A liquid chromatographic apparatus comprising:
   a. a chromatographic column having an inlet and an outlet;
   b. detector means in operable communication with the outlet of said column;
   c. a first carrier liquid reservoir containing a first carrier liquid;
   d. a second carrier liquid reservoir containing a second carrier liquid having a composition different from the composition of said first carrier liquid;
   e. means for introducing said first carrier liquid under high pressure to the inlet of said column;
   f. means for introducing a liquid sample to the inlet of said column; and
   g. carrier valve means connected between said column inlet and said means for introducing said first carrier, said carrier valve means having a chamber of fixed volume, for said second carrier, including actuating means, for normally flowing said first carrier liquid through said valve means and for normally flowing said second carrier liquid from said second reservoir through said chamber for said second carrier and upon actuation of said carrier valve means for flowing said first carrier liquid through said carrier chamber thereby propelling at least a portion of said second carrier liquid into said column.

2. The apparatus of claim 1 wherein said means for introducing said first carrier liquid under high pressure comprises a constant pressure pump.

3. The apparatus of claim 1 wherein said means for introducing said first carrier liquid under high pressure comprises a constant volume pump.

4. The apparatus of claim 1 wherein said sample introducing means is a sample valve means having a sample chamber of predetermined volume, including actuating means, for normally flowing said carrier liquid through said sample valve means and for normally flowing a liquid stream to be sampled through said sample chamber and upon actuation of said sample valve means for flowing said carrier liquid through said sample chamber thereby carrying a sample portion of said stream into said column.

5. The apparatus of claim 1 wherein a low pressure pump is disposed between said second reservoir and said chamber for said second carrier, whereby said low pressure pump maintains said chamber for said second carrier liquid full.

6. The apparatus of claim 1 wherein said carrier valve means is disposed between said first carrier introducing means and said sample introducing means.

7. The apparatus of claim 1 wherein said carrier valve means is disposed between said sample introducing means and said column inlet.

8. The apparatus of claim 6 wherein said sample valve means and said carrier valve means are multi-port valves having six ports and first and second operating positions, with port one connected to port two, port three to port four and port five to port six in said first position, and with port one connected to port six, port two to port three and port four to port five in said second position; wherein in said sample valve means said port two is in operable communication with the inlet of said column, said port five is connected to a source of said liquid stream to be sampled, said sample chamber is connected between said port six and said port three and said port one is connected with port two of said carrier valve means; and wherein in said carrier valve means, said port five is connected to a source of said second carrier liquid, said carrier chamber is connected between said port six and said port three and said port one is in operable communication with said first liquid carrier introducing means.

9. The apparatus of claim 7 wherein said sample valve means and said carrier valve means are multi-port valves having six ports and first and second operating positions, with port one connected to port two, port three to port four and port five to port six in said first position, and with port one connected to port six, port two to port three and port four to port five in said second position; wherein in said carrier valve means, said port two is in operable communication with the inlet of said column, said port five is connected to a source of said second carrier liquid, said chamber for said second carrier is connected between said port six and said port three, and said port one is connected with said port two of said sample valve means; and wherein in said sample valve means said port five is connected to a source of said liquid stream to be sampled, said sample chamber is connected between said port six and said port three, and said port one is in operable communication with said first liquid carrier introducing means.

10. The apparatus of claim 1 additionally comprising at least one means for introducing at least one further carrier liquid having a composition different from the compositions of said first carrier liquid and said second carrier liquid, disposed between said first carrier introducing means and said column inlet.

11. A liquid chromatographic process for the analysis of a liquid sample which comprises introducing a first carrier liquid at a constant flow rate into a chromatographic column and through a detecting means for detecting a property of the liquid flowing therethrough, introducing a specific amount of a liquid sample into said column thereby diluting at least a portion of said sample through said column and said detecting means, and after a predetermined interval, introducing a second carrier liquid into said column in place of said first carrier liquid thereby eluting the remainder of said liquid sample through said column and said detector means, wherein said second carrier liquid is introduced between said column inlet and said first carrier liquid, whereby said first carrier liquid propels said second carrier liquid into and through said column.

12. The method of claim 11 wherein said second carrier is incrementally introduced and wherein said first carrier and said second carrier are intimately mixed, thereby producing a composition intermediate between said first carrier and said second carrier.

13. The method of claim 12 wherein the time ratio between said first carrier and said second carrier is changed over the time period of the analysis, thereby producing a smooth gradient from said first carrier to said second carrier.

* * * * *